United States Patent
Jolley

(10) Patent No.: US 6,821,257 B1
(45) Date of Patent: Nov. 23, 2004

(54) METHOD AND APPARATUS FOR EVALUATING BACK FLEXIBILITY

(76) Inventor: Jeffrey Jolley, 4624 E. Garnet Cir., Mesa, AZ (US) 85206

(*) Notice: Subject to any disclaimer, the term of this patent is extended or adjusted under 35 U.S.C. 154(b) by 233 days.

(21) Appl. No.: 10/155,396

(22) Filed: May 28, 2002

(51) Int. Cl.$^7$ .......................... A61B 5/103; A61B 5/117
(52) U.S. Cl. ........................................ 600/595
(58) Field of Search .............................. 600/595, 594, 600/587; 33/512

(56) References Cited

U.S. PATENT DOCUMENTS

| | | |
|---|---|---|
| 4,655,227 A | 4/1987 | Gracovetsky |
| 4,858,126 A | 8/1989 | Croce |
| 4,882,677 A | 11/1989 | Curran |
| 4,971,069 A | 11/1990 | Gracovetsky |
| 5,188,121 A * | 2/1993 | Hanson ...................... 600/594 |
| 5,224,035 A | 6/1993 | Yamashita |
| 5,582,186 A | 12/1996 | Wiegand |
| 5,647,375 A | 7/1997 | Farfan de los Godos |
| 5,662,122 A | 9/1997 | Evans |
| 5,848,594 A | 12/1998 | Matheson |
| 5,997,440 A | 12/1999 | Hanoun |
| 6,056,671 A | 5/2000 | Marmer |
| 6,152,890 A * | 11/2000 | Kupfer et al. .............. 600/595 |
| 6,159,168 A | 12/2000 | Warner |
| 6,165,143 A | 12/2000 | van Lummel |
| 6,168,569 B1 | 1/2001 | McEwen |

* cited by examiner

Primary Examiner—Max F. Hindenburg
Assistant Examiner—Brian Szmal
(74) Attorney, Agent, or Firm—LaValle D. Ptak

(57) ABSTRACT

A system and method is disclosed for evaluating the likelihood of a person to subsequently develop a back injury on a job which requires some medium to heavy lifting and a variety of back movements. The system and method include measuring various back movements, namely flexion, extension, side bending, rotation and trunk flexibility, and then comparing each measurement against a pre-established threshold. Failing to meet the threshold in any one of the measurements disqualifies a person for the job under consideration.

14 Claims, 5 Drawing Sheets

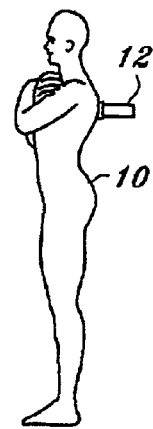
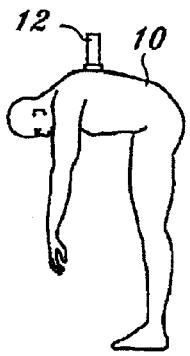
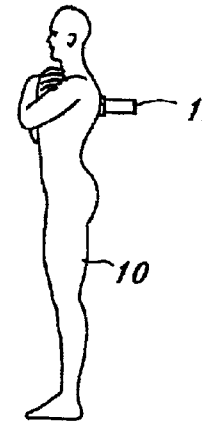
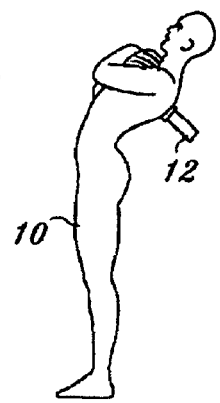
*Fig. 1A*  *Fig. 1B*  *Fig. 2A*  *Fig. 2B*
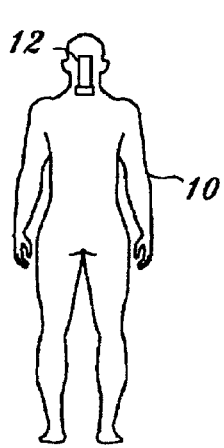
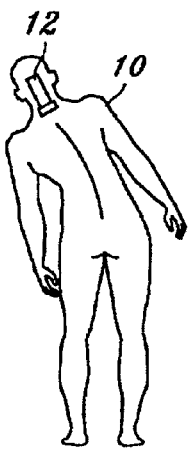
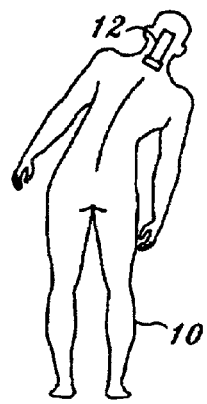
*Fig. 3A*  *Fig. 3B*  *Fig. 3C*
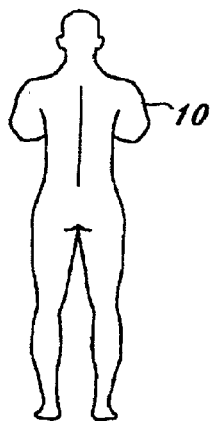
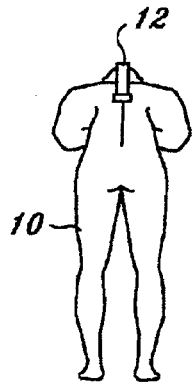
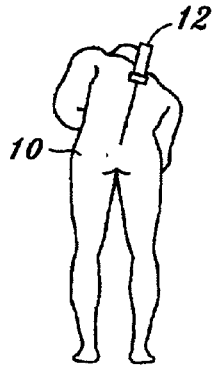
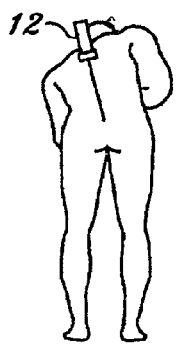
*Fig. 4A*  *Fig. 4B*  *Fig. 4C*  *Fig. 4D*

METHOD AND APPARATUS FOR EVALUATING BACK FLEXIBILITY

BACKGROUND

Significant advances have been made in the ergonomics of work stations and in the education of workers for jogs requiring substantial amounts of lifting, and a variety of back movements while on the job. Even so, increasing significant costs in terms of employee injuries, medical expenses, and workmen's compensation continue to be incurred by employers. In fact, back related injuries and their related costs to employers for workmen's compensation currently exceed sixty billion dollars annually in the United States alone. Such figures exclude indirect costs, in the form of lost productivity of injured employees, recruitment and training of replacement workers, and allowing for light duty for injured employees, not to mention the pain and disability incurred by injured employees.

Systems and methods have been developed for assessing and evaluating the degree of movement of the human spine (indicative of past injuries or a tendency to incur future injuries). Such systems and methods include the measuring of various parameters, such as flexion, extension, side bending, rotation, and the like. Patents which use devices and methods for measuring some of these parameters compared to a standard for permitting evaluation are disclosed in the United States patents to Croce No. 4,858,126; Gracovetsky No. 4,971,069; Farfan de los Godos No. 5,647,375; and Marmer No. 6,056,671.

The United States patent to Hanoun No. 5,997,440 is directed to a device for measuring various degrees of motion of the cervical muscles through head movement only. The measurements are obtained and provided to a computer for comparison with a pre-established standard or model. The United States patent to Gracovetsky No. 4,655,227 is directed to an automatic comparison system and method for measuring movement of the spine utilizing a mathematical model, and measuring the angle of flexion while the patient is undergoing specified exercises. This is accomplished through the use of sensors placed on the patient, to provide an automatic readout to a computer for the evaluation.

Another approach for measuring various motor activities performed by an individual is disclosed in the United States patent to VanLummel No. 6,165,143. This patent discloses a system providing a comparative readout of different parameters as the patient performs pre-assigned tasks.

None of the foregoing patents, however, is directed to a methodology and system for providing a comprehensive analysis of a number of back movement measurements, all of which are compared to a pre-established known threshold or standard for determining, in advance, the potential for a worker or a job applicant to incur a back injury for specific jobs requiring lifting and substantial back movement. It is desirable to provide a method and system for use by employers which provides a comprehensive analysis of the potential of a worker to subsequently develop back injuries on jobs requiring lifting and back movement.

SUMMARY OF THE INVENTION

It is an object of this invention to provide a method for evaluating the capability of a person for performing various physical tasks.

It is another object of this invention to provide a method and apparatus for objectively determining the potential of a person for developing subsequent back injuries in the performance of certain tasks.

It is an additional object of this invention to provide a method and apparatus for objectively passing or rejecting employees for certain jobs based on measurements of a plurality of back motions.

It is a further object of this invention to provide a method and apparatus for evaluating the capability of a person to perform physical tasks by providing a standard reference threshold value for predetermined physical characteristics, measuring the predetermined physical characteristics of a person, and comparing the measured characteristics with the standard references. The comparison then is utilized to provide a pass/fail determination of the person to perform the physical tasks based on the results obtained by comparing the measured value with the reference value.

BRIEF DESCRIPTION OF THE DRAWINGS

FIGS. 1A and 1B illustrate one type of measurement used with a preferred embodiment of the invention;

FIGS. 2A and 2B illustrate another type of measurement used in conjunction with a preferred embodiment of the invention;

FIGS. 3A, 3B and 3C illustrate a third type of measurement used in conjunction with a preferred embodiment of the invention;

FIGS. 4A, 4B, 4C and 4D illustrate a fourth type of measurement used in conjunction with a preferred embodiment of the invention;

DETAILED DESCRIPTION

Reference now should be made to the drawings in which the same reference numbers are used throughout the different figures to designate the same or similar components. FIGS. 1 through 5 illustrate various body positions which are used in making the measurements utilized in conjunction with a preferred embodiment of the invention to evaluate back flexibility. In all of these figures, sketches of a person 10 are shown in different positions used to obtain the different measurements used with a preferred embodiment of the invention.

In FIGS. 1 through 4, a digital inclinometer 12 is illustrated for obtaining angular measurements associated with a preferred embodiment of the invention. Digital inclinometers of any suitable commercial type may be used for the inclinometer 12 to effectively measure a range on angle of motion. The inclinometer 12 used with the preferred embodiment of the invention provides a digital readout, which measures degrees of angular movement from a start or zero position to a maximum position. Angular measurements may be taken with instruments other than a digital inclinometer; but such an instrument is ideal for the preferred embodiment of the invention.

Figure 7A:
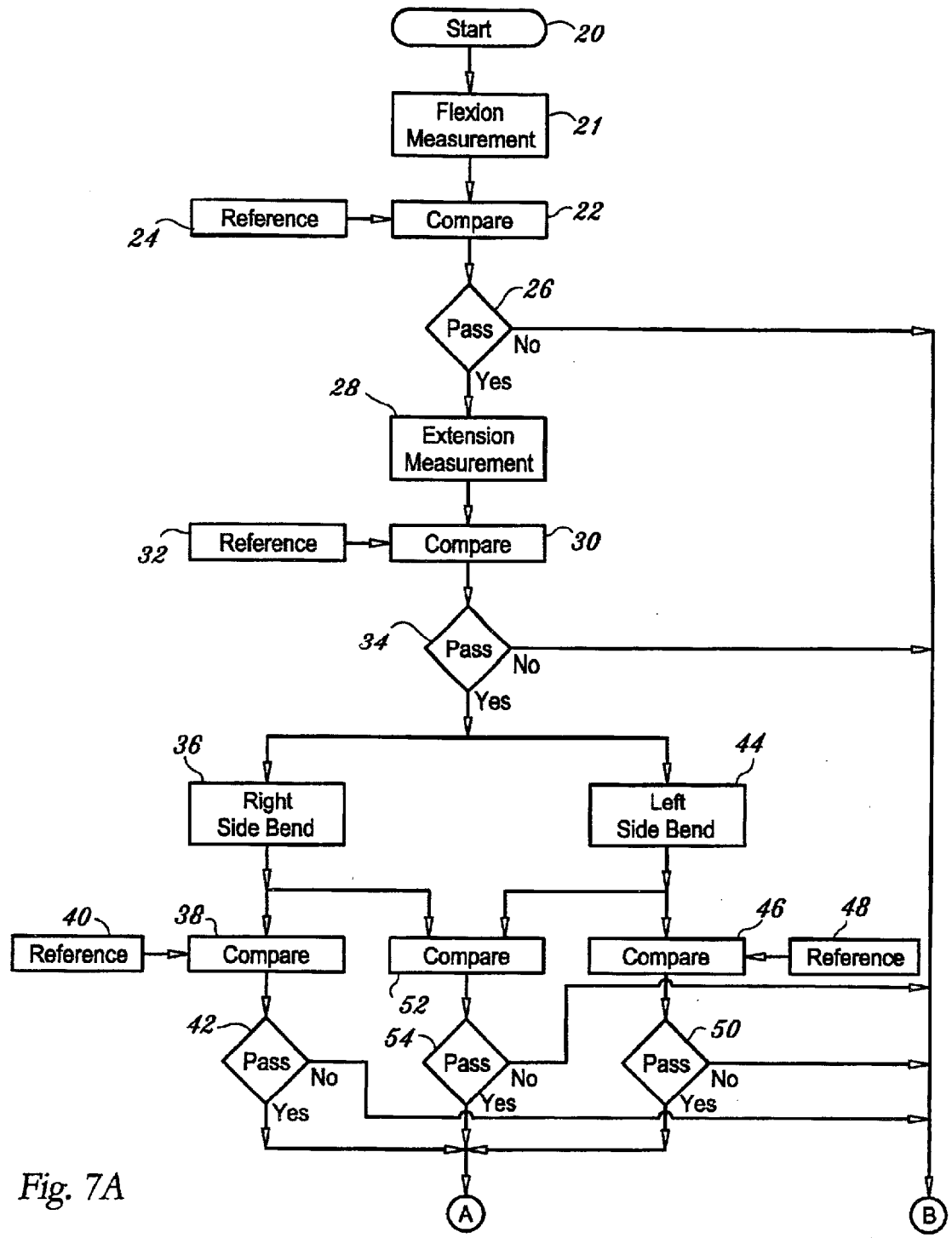
FIGS. 7A and 7B are a flow chart of a preferred embodiment of the invention.
Figure 7B:
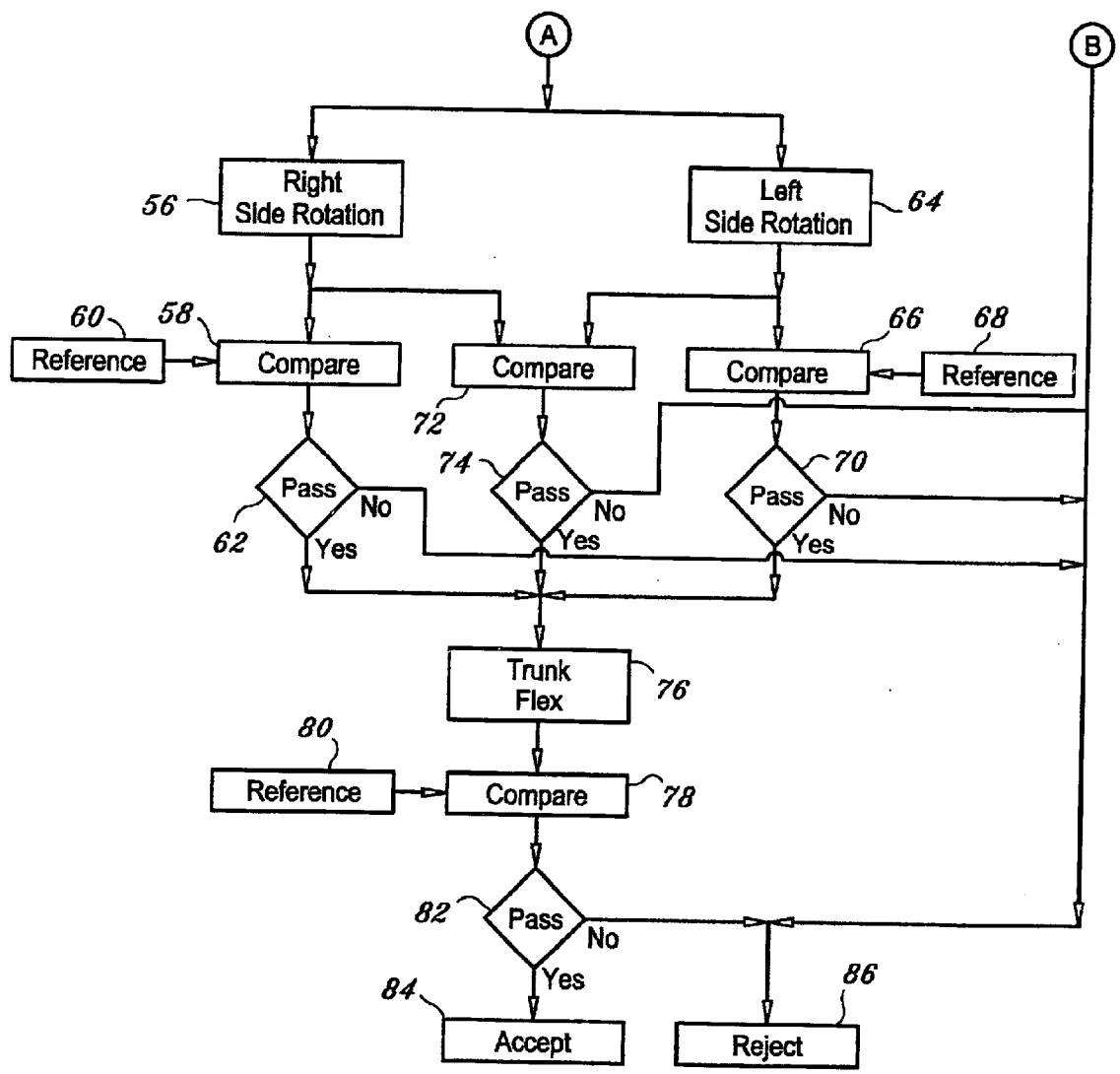

The illustrations of FIGS. 1 through 5 should be considered in conjunction with the flow chart of FIG. 7 for an understanding of the preferred embodiment of the method and apparatus for evaluating back flexibility, primarily for the purpose of determining whether an employee or prospective employee is capable of undertaking lifting and back movement associated with employment requiring bending and rotating of the back while manipulating or lifting various weights. The purpose of the preferred embodiment of the invention is to eliminate; from jobs requiring physical stress of the back, employees or prospective employees who might, as a result of weaknesses of the back, sustain back injuries while on the job.

The evaluation method and system begins, as shown in FIG. 7, at a start 20. The first measurement which is taken is the flexion measurement, at 21; and the manner in which this is done is illustrated in FIGS. 1A and 1B. The person 10 first stands with feet together, as illustrated in FIG. 1A. The digital inclinometer 12 is placed between the shoulder blades, in the position shown in FIG. 1A, and the angle display (or digital readout to a computer) is set to zero by the operator. The person 10 then is instructed to bend forward at the waist, as shown in FIG. 1B, while keeping knees locked. This provides flexion (forward bending) back motion.

When the person 10 is flexed as far forward as possible, the reading is taken from the digital inclinometer 12, in the position shown in FIG. 1B. This may be accomplished by locking a display on the digital inclinometer, or by providing the output directly to a computer for use with the system. For best results, the measurements described above and shown in FIGS. 1A and 1B are repeated two more times; and an average of the measurements is taken for a final reading. This is true of all of the other measurements which are described subsequently in conjunction with FIGS. 2 through 5, that is, an average of three readings is taken for each of the measurements used with the system.

The flexion measurement taken at 21 then is compared at 22 with a pre-established reference at 24, as shown in FIG. 7. For flexion measurements, the threshold or norm is 90° range of motion, which generally is indicated by a comparison of FIGS. 1A and 1B.

Flexion is not a particularly good indicator of low back dysfunction, because there is a complex movement which occurs during flexion and extension measurements. Only approximately 72° is what would be called true lumbar range of motion, while the remainder is pelvic rotation. Persons with low back dysfunction frequently show extreme flexibility during flexion. If a person, however, has less than a 90° range of motion (the threshold established by the reference 24), the comparison at 22 indicates, at 26, that the flexion range of motion fails ("No" at. 26). If greater than 90° range of motion is measured, however, the person passes at 26, as shown in FIG. 7.

The next test or measurement is shown in FIGS. 2A and 2B. This is extension measurement. Extension is a better indicator of low back dysfunction, due to the fact that facet joints of the spine are forced together during extension. As with flexion, a threshold measurement is established as a reference at 32 (FIG. 7). For the purposes of the preferred embodiment of the invention, this threshold is determined to be anything less than 30° range of motion.

To obtain a measurement of extension, the person 10 once again stands with feet together. The arms are crossed across the chest, with the hands on the shoulders; and the knees are locked. Once this done, as shown in FIG. 2A, the digital inclinometer 12 is set to its zero or start position as described previously in conjunction with FIG. 1A. The person 10 then is instructed to bend back as far as he or she can. This is indicated in FIG. 2B. Once the maximum back bending extension has taken place, a reading is taken by the digital inclinometer 12 (at 28 in FIG. 7), as shown at FIG. 2B; and a comparison is made at 30 with the reference at 32 to determine at 34 whether there is a pass or fail of the extension measurement. If the extension is greater than 30°, the determination is a pass (Yes). If the extension is less than 30°, the decision at 34 is a fail (No), as indicated in FIG. 7.

The next measurement actually constitutes a pair of similar measurements, right-side bending and left-side bending, as indicated at 36 and 44 in FIG. 7. Side bending is considered a fairly reliable indicator of low back dysfunction. In addition to taking side bending measurements for both left and right sides, a comparison between the two sides also is made. For this test, the reference for the side bending for both left and right, as shown in the references 40 and 48 of FIG. 7, is a threshold of 25°; and a fail (No) indication is made if there is less then 25° range of motion. In addition, a comparison is made at 52 to determine the amount of difference in the bending of the two sides.

The measurements are taken as shown in FIGS. 3A, 3B and 3C. In FIG. 3A, the person 10 is told to stand erect with arms down at the sides. The digital inclinometer 12 is placed on the mid-line of the back, resting it on the shoulders as indicated in FIG. 3A. As described previously in conjunction with FIGS. 1A and 2A, the inclinometer 12 is set to a zero reading when it is in the position shown in FIG. 3A.

The first reading shown in FIG. 3B is for left-side bending. The person is asked to slide their left hand down the leg and bend to the left while ensuring that there is no flexing forward, and strictly bending to the side, as shown in FIG. 3B. The inclinometer base is maintained against the shoulders as they bend to the side, as shown in FIG. 3B. Once the maximum bend has been achieved, as illustrated in FIG. 3B, the measurement at 44 of the left-side bend is compared at 46 (FIG. 7) with the reference 48 described previously. For the preferred embodiment of this invention, it has been determined that the side bending threshold is 25°. Thus, the test is passed if side bending exceeds this threshold. Consequently, if the left side bend at the comparison 46 is greater than 25°, an indication is made at 50 that the test is passed (Yes). If it is less than 25°, the decision at 50 indicates a failure or a "no" response.

A similar measurement is made for the right-side bending, as shown in FIG. 3C. The right-side bend at 36 is compared at 38 with the reference 40; and as with the left-side bending, if the right side bend is greater than 25°, it is indicated as a pass at 42. If it is less than 25°, a failure is indicated with a "no" response at 42.

In addition to the measurements made above, the output of the digital inclinometer 12 for both the left-side bend at 44 and the right-side bend at 36, is compared at 52 to determine whether the measurements from the two different side bendings differ by more than 10° when one side is compared to the other. The output of the comparator 52 is indicated as a pass or fail at 54, with a pass (Yes) indicated-if there is less than 10° difference between the two measurements, and a failure (No) if there is a greater than 10° difference between the left bending and right bending measurements.

The next set of measurements is shown as right-side rotation 56 and left-side rotation 64 in FIG. 7. The manner in which these measurements are taken is shown in FIGS. 4A through 4D. Rotation is also considered to be a good indication of low back dysfunction. In most cases, this is where, if there is a low back dysfunction, the greatest differences between the left rotation and right rotation will occur.

To take the rotation measurement, the person 10 stands erect with arms crossed, resting the right hand on the left shoulder and the left hand on the right shoulder (FIG. 4A). The person then bends at the waist so the trunk is parallel to the ground, or horizontal, as in the case of the flexion measurement shown in FIG. 1B; Once this position is reached, the digital inclinometer 12 is placed with the base of the inclinometer between the shoulder blades, as shown in FIG. 4B. In this position, the inclinometer, reading is set to zero, as described previously.

The left rotation (64 in FIG. 7) measurement is taken next. This is done by having the person rotate to the left, as shown in FIG. 4C, making sure that the person drops the right shoulder toward the ground. The base of the inclinometer 12 is maintained between the shoulder blades along the midline as this rotation takes place, as illustrated in FIG. 4C. When the end point of the rotation is reached, the measurement is taken; and the left rotation is compared with the reference 68 at 66. For rotation, it has been determined that if there is less than 30° range of motion, an indication of an actual or potential lower back dysfunction is made. If so, at the comparison 66, the decision is made at 70 to pass (Yes) the test if greater than 30° range of motion takes place, or fail (No) if less than 30° range of motion takes place.

A similar measurement is made for right rotation, as shown in FIG. 4D. The comparison of right rotation 56 is made at 58, with the reference 60. If less than 30° range of motion takes place, the decision at 62 is no or a failure. If greater than 30° rotation takes place, the person passes the test (Yes), as shown at 62.

As with the right and left side bending, right and left-side rotation measurements also are compared at 72. If the difference between the two measurements at 72 is less than 10°, the person passes the test at 74. If the difference between the left-side and right-side rotation is greater than 10°, the decision at 74 is a failure or "no" output, as shown in FIG. 7.

Figure 6:
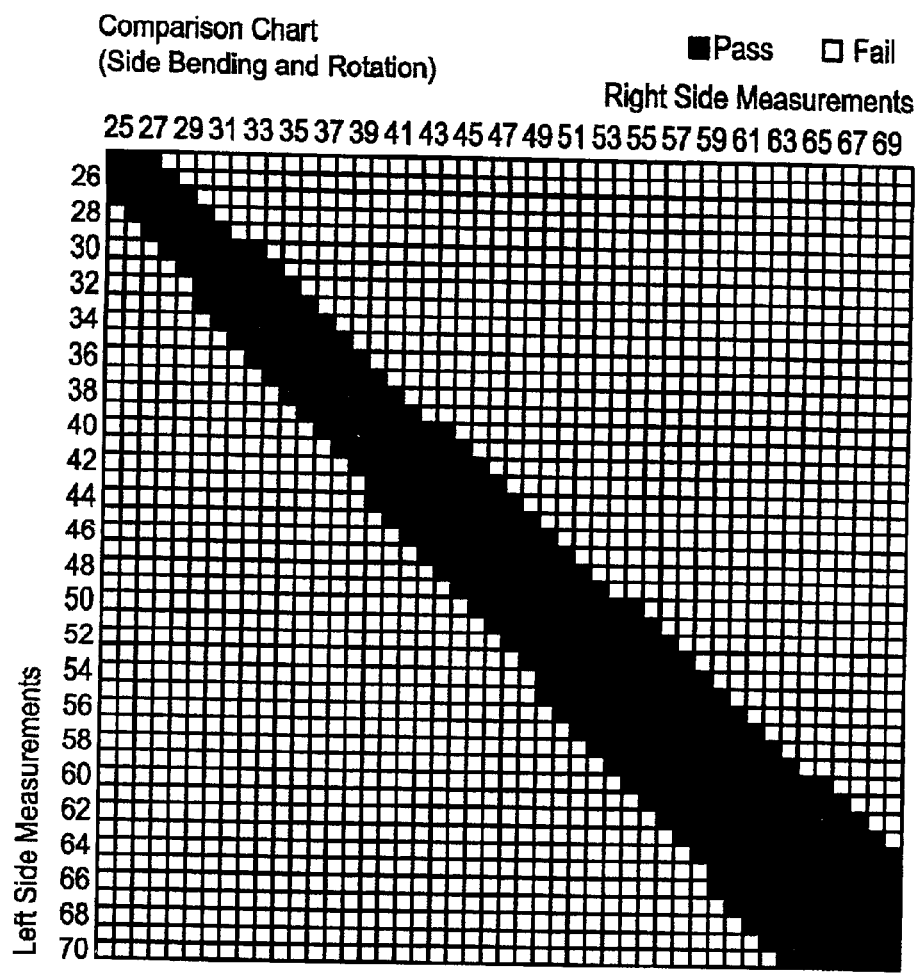
FIG. 6 is a comparison chart used in conjunction with the preferred embodiment of the invention.

FIG. 6 is a comparison chart useful in assessing the measurements which are made for side bending and rotation, as described above in conjunction with FIGS. 3A to 3C and 4A to 4D. In FIG. 6, the right-side measurements are provided in the vertical columns and the left-side measurements are provided in the horizontal columns, with the passing range of the two measurements blocked in the darker squares providing a diagonal from the upper left to the lower right of the chart of FIG. 6. The failing measurements, indicated by a "no" output from the decision blocks 42, 50, 54, 62, 70 and 74 are shown in the open or lighter squares comprising the remainder of FIG. 6. FIG. 6 is a convenient way of obtaining a quick visual indication of the pass/fail results of these measurements.

The final measurement which is taken for determining the probability of potential future back injuries of a person undergoing work of the type described previously, is trunk flexibility at 76, in FIG. 7. Trunk flexibility is compared to the averages for the age and the sex of the person undergoing the test. This is the only test which takes into consideration age and sex. Age and sex are of no consequence in the tests which have been described previously. The trunk flexibility test is failed if the person 10 is below average in comparison with the average measurements for that person's age and sex, as set forth on the following table:

TABLE 1

| Men's Score by Age | | Women's Score by Age | |
| --- | --- | --- | --- |
| Age | Average | Age | Average |
| 18–25 | 15–16 | 18–25 | 18–19 |
| 26–35 | 15–16 | 26–35 | 18 |
| 36–45 | 13–15 | 36–45 | 16–17 |
| 45–55 | 12–13 | 45–55 | 15–16 |
| 56–65 | 10–12 | 56–65 | 15 |

Figure 5A:
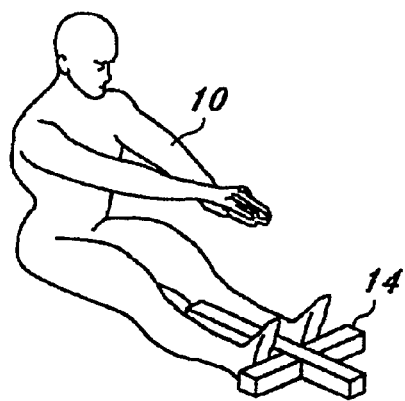
FIGS. 5A and 5B illustrate another measurement used in conjunction with a preferred embodiment of the invention.
Figure 5B:
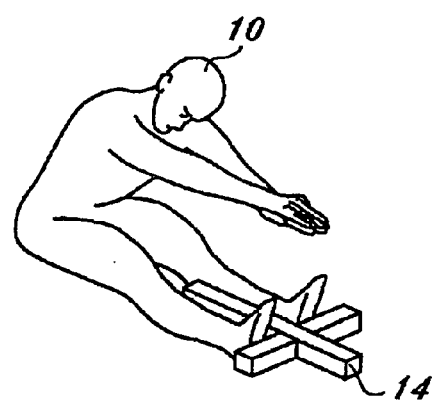

Reference now should be made to FIGS. 5A and 5B for the manner in which the trunk flexibility test is made. The tool which is used to measure trunk flexibility is an elongated measuring tool 14 having a first elongated portion, which extends between the legs of the person 10 with the person sitting on the ground. Measuring indicia, as indicated in FIGS. 5A and 5B, extend along the length of this first portion. Typically, this indicia is in the form of one inch intervals. A cross bar or second portion, again shown clearly in FIGS. 5A and 5B, extends across the elongated portion and is designed to rest against the bottoms of the feet of the person undergoing measurements. For the preferred embodiment of the invention, the indicia is at 15 inches at the point where the cross bar resting against the feet of the person 10 is located. The numbering then extends in one inch increments, upwardly toward the right-hand end as viewed in FIGS. 5A and 5B, and downwardly from fifteen inches toward the person seated, as shown in FIG. 5A.

To undertake the trunk flexibility test 76 (FIG. 7), the tool 14 is placed as shown in FIG. 5A; and the person 10 places his or her feet against the instrument. Crossing one hand over the other, the person then is instructed to reach forward as far as possible, holding the position for about five seconds. The knees are to be locked; and no bouncing is to take place at the end. Again, as with the tests shown in FIGS. 1 through 4, three different readings ideally are taken, with the average of the three readings being considered the test reading. As shown in FIG. 5B, the distance to which the hands extend over the measurement indicia on the portion 14 is recorded, either automatically or manually. A comparison is made at 78, with the reference 80 to determine whether the average is attained or exceeded. As noted previously, the reference at 80 is varied in accordance with the age and sex of the person undergoing the test. If the reference is met or exceeded, a pass (Yes) decision is made at 82. Otherwise, the decision at 82 is a fail (No) indication.

As shown in FIG. 7, if all of the tests are passed, the decision is shown at 84 as an acceptance. Basically, this decision means that the person is capable of undertaking physical activity which requires a significant amount of back motion and lifting and moving of relatively heavy objects. As is readily apparent from an examination of the flow chart of FIG. 7, any one of the decisions made at the various tests which results in a "no" from the corresponding pass/fail decision point results in a rejection at 86 of the person for employment or continued employment in a job requiring substantial back motion and lifting.

Although the flow chart of FIG. 7 shows the acceptance at 84 as being the result of sequential measurement, the order in which the various measurements or tests are made can be varied from the order described above in conjunction with FIG. 7, since the reject decision 86 occurs if any one of the tests fails. For a complete assessment, however, all of the tests should be made; so that a clear analysis of a variety of potential problems is achieved.

Figure 8:
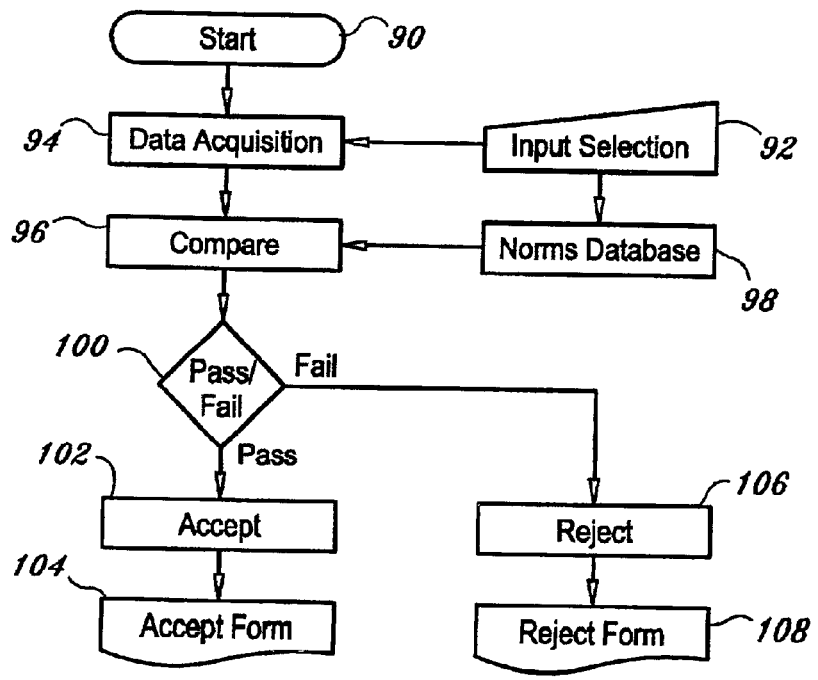
FIG. 8 is a block diagram of a system of a preferred embodiment of the invention.

FIG. 8 is a block diagram of the components of a fully automated system for achieving the methodology described above in conjunction with FIG. 7, and with the specific tests which are shown as performed in FIGS. 1 through 5. In FIG. 8, the system is started at 90; and the input selection may be entered by means of a keyboard or other input 92 for data acquisition at 94. The particular input selection at 92 also is supplied to a database 98, which stores the comparison or reference indications. These are correlated with the specific input selection made at 92 and supplied through the data acquisition at 94. The acquisition data is compared in a comparator at 96, with the reference thresholds stored in the database 98. The pass/fail decision is made at 100 from the output of the comparator 96, much in the same way as described previously in conjunction with the various pass/fail decisions made after the different tests described previously in conjunction with FIG. 7.

If a pass decision is made, it is accepted at 102; and an acceptance form 104 is printed showing that the person has passed all of the various tests. On the other hand, if there is a failure, this is supplied to a reject output 106, which prints the reject form 108 indicating the failure, and, if desired, the specific test(s) and results for subsequent analysis and review.

The foregoing description of a preferred embodiment of the invention is to be considered as illustrative and not as limiting. Various other changes and modifications will occur to those skilled in the art for performing substantially the same function, in substantially the same way, to achieve substantially the same result, without departing from the true scope of the invention as defined in the appended claims.

What is claimed is:

1. A method for evaluating the capability of a person to perform a physical task including the steps of:

providing a standard reference threshold value for a predetermined physical characteristic;

measuring the predetermined physical characteristic of a person to obtain a measured value of the predetermined physical characteristic;

comparing the measured value with the reference threshold value; and providing a pass/fail determination of the person to perform a physical task based on the results obtained by comparing the measured value with the reference threshold value.

2. The method according to claim 1 wherein the predetermined physical characteristic is a range of motion of the back of a person.

3. The method according to claim 2 wherein the range of motion comprises motion selected from the group consisting of: flexion, extension, side bending, and rotation.

4. The method according to claim 1 wherein the step of providing a standard reference threshold value is for a first predetermined physical characteristic, and wherein the step of measuring is the step of measuring the first predetermined physical characteristic and further including the steps of providing a standard reference threshold value for a second predetermined physical characteristic and measuring the second predetermined physical characteristic of a person to obtain a measured value of the second predetermined physical characteristic; and comparing the second measured value with the second reference threshold value wherein the step of providing a pass/fail determination is based on the results obtained by both of the comparing steps.

5. The method according to claim 4 wherein the first predetermined physical characteristic is flexion motion of the back and the second predetermined characteristic is extension motion of the back.

6. The method according to claim 4 wherein the first predetermined physical characteristic is side bending to the left, and the second predetermined physical characteristic is side bending to the right.

7. The method according to claim 4 wherein the first predetermined physical characteristic is rotation of the lower back to the right, and the second predetermined physical characteristic is rotation of the back to the left.

8. The method according to claim 3 wherein the step of providing a standard reference threshold value is for a first predetermined physical characteristic, and wherein the step of measuring is the step of measuring the first predetermined physical characteristic and further including the steps of providing a standard reference threshold value for a second predetermined physical characteristic and measuring the second predetermined physical characteristic of a person to obtain a measured value of the second predetermined physical characteristic; and comparing the second measured value with the second reference threshold value wherein the step of providing a pass/fail determination is based on the results obtained by both of the comparing steps.

9. The method according to claim 2 wherein the step of providing a standard reference threshold value is for a first predetermined physical characteristic, and wherein the step of measuring is the step of measuring the first predetermined physical characteristic and further including the steps of providing a standard reference threshold value for a second predetermined physical characteristic and measuring the second predetermined physical characteristic of a person to obtain a measured value of the second predetermined physical characteristic; and comparing the second measured value with the second reference threshold value wherein the step of providing a pass/fail determination is based on the results obtained by both of the comparing steps.

10. Apparatus used in the evaluation of the capability of a person to perform various physical tasks including in combination:

a device for measuring a plurality of predetermined physical characteristics of a person to obtain measured values of each of the plurality of physical characteristics;

a reference database of stored threshold values corresponding to the desired thresholds for each of the plurality of predetermined physical characteristics;

a comparator for comparing each of the measured values of each of the plurality of predetermined physical characteristics with the stored threshold values for the corresponding physical characteristics to provide an output for each of the plurality of physical characteristics indicative of whether the measured value is less than or greater than the stored threshold value corresponding to that physical characteristic; and means for selecting, in sequential order, the different predetermined physical characteristics to be measured and compared in the comparator.

11. The apparatus according to claim 10 wherein the physical characteristics are each different rotational characteristics of the back of a person, and the apparatus for providing the measurement of the characteristics is an inclinometer.

12. The apparatus according to claim 11 wherein the inclinometer is a digital inclinometer.

13. The apparatus according to claim 10 wherein the physical characteristics are each different rotational characteristics of the back of a person, and the apparatus for providing the measurement of the characteristics is an inclinometer.

14. The apparatus according to claim 13 wherein the inclinometer is a digital inclinometer.

* * * * *